United States Patent [19]

Elder et al.

[11] 4,233,513
[45] Nov. 11, 1980

[54] GAS ANALYZER

[75] Inventors: William L. Elder, Richmond; Kevin G. Williams, Pinole; Irvin G. Burough, Walnut Creek, all of Calif.

[73] Assignee: Andros Incorporated, Berkeley, Calif.

[21] Appl. No.: 948,674

[22] Filed: Oct. 5, 1978

[51] Int. Cl.[2] .......................... G01J 1/00; G01N 21/26
[52] U.S. Cl. .................................. 250/343; 250/352
[58] Field of Search ............... 250/343, 344, 346, 351, 250/352

[56] References Cited

U.S. PATENT DOCUMENTS

| | | | |
|---|---|---|---|
| 3,793,525 | 2/1974 | Burch et al. | 250/343 |
| 3,904,880 | 9/1975 | Benz et al. | 250/343 |
| 3,953,734 | 4/1976 | Dimeff | 250/343 |
| 4,013,260 | 3/1977 | McClathie et al. | 250/343 |

Primary Examiner—Davis L. Willis
Assistant Examiner—Janice A. Howell

Attorney, Agent, or Firm—Fitch, Even, Tabin, Flannery & Welsh

[57] ABSTRACT

A gas analyzer of the non-dispersive infrared type is described. An infrared beam passing through a sample cell containing a gas mixture to be analyzed is detected. The resulting electrical signals are processed to produce an output indicating the concentration of the constituents of the gas mixture in the sample cell. The gas analyzer includes provision for temperature stabilizing both a rotary filter wheel and the detector, and for compensating the output of the signal processor for variation in the absorption characteristics of gas with temperature. The emissivity characteristic of the infrared energy source substantially compensates for wavelength dependence of the detector response. The motor drive for the rotary filter wheel is servo-controlled in accordance with synchronizing pulses developed directly from the detector output.

9 Claims, 5 Drawing Figures

GAS ANALYZER

This invention relates to gas analyzers and, more particularly, to an improved gas analyzer of the non-dispersive infrared type.

Non-dispersive infrared gas analyzers typically utilize an infrared source to produce and direct infrared energy through an unknown gas mixture contained in a sample cell. The energy passing through the sample cell is detected and electrical signals are produced representative thereof. These signals are processed to produce an output indicating the concentration of the constituents of the gas in the sample cell.

Such gas analyzers utilize the principle that various gases exhibit substantially increased absorption characteristics at specific wavelengths in the infrared radiation spectrum. A gas analyzer of this type is shown and described in U.S. Pat. No. 4,013,260, McClatchie et al, issued Mar. 22, 1977, and assigned to the assignee of the present invention. Another type of non-dispersive infrared gas analyzer is shown and described in U.S. Pat. No. 3,953,734, Dimeff, issued Apr. 27, 1976, and assigned to the United States of America.

The accuracy of gas analyzers of this general type may be substantially affected by a number of factors. For example, where a rotating filter wheel is utilized to interpose in succession one or more filters in the path of the infrared energy, the spectral properties of the system may change significantly with ambient temperature, as a result of, among other things, varying transmission characteristics of the interference filters, varying output of the detector with temperature, and variation in the absorption characteristics of the gases themselves with temperature. The accuracy of a gas analyzer of this general type may also be affected because the response of the detector may be dependent on the wavelength of the energy which is impinging upon it. Accuracy may also be further affected as a result of variation in the rotary speed of the filter wheel.

It is an object of the present invention to provide an improved gas analyzer of the non-dispersive infrared type.

Another object of the invention is to provide an improved gas analyzer which is stabilized against variation in output due to changes in ambient temperature.

Another object of the invention is to provide an improved gas analyzer wherein changes in output as a result of wavelength dependence are minimized.

A further object of the invention is to provide an improved gas analyzer wherein the rotary speed of the filter wheel is closely controlled.

Other objects of the invention will become apparent to those skilled in the art from the following description, taken in connection with the accompanying drawings wherein.

Very generally, the gas analyzer of the invention comprises a sample cell for containing a gas mixture to be analyzed, means for producing and directing infrared energy through the sample cell, and means for detecting the infrared energy passing through the sample cell. The electrical signal produced from the detected infrared energy is processed to produce an output indicating the concentration of the constituents of the gas of the sample cell. A rotary filter wheel, which successively and repetitively positions at least one filter in the path of the infrared energy, is enclosed by a housing and is maintained at a substantially constant temperature. The infrared energy source has an emissivity characteristic which varies in a way that at least partially compensates for wavelength dependence of the response of the detector. The detector is temperature-stabilized by thermoelectric means which either heat the temperature up or cool the temperature down with respect to the ambient temperature. Temperature compensation means are also provided in the signal processor to compensate for variation in the absorption characteristics of gas with temperature. The motor which drives the rotary filter wheel is servo-controlled by synchronizing pulses derived directly from the detected infrared signal.

Figure 1:
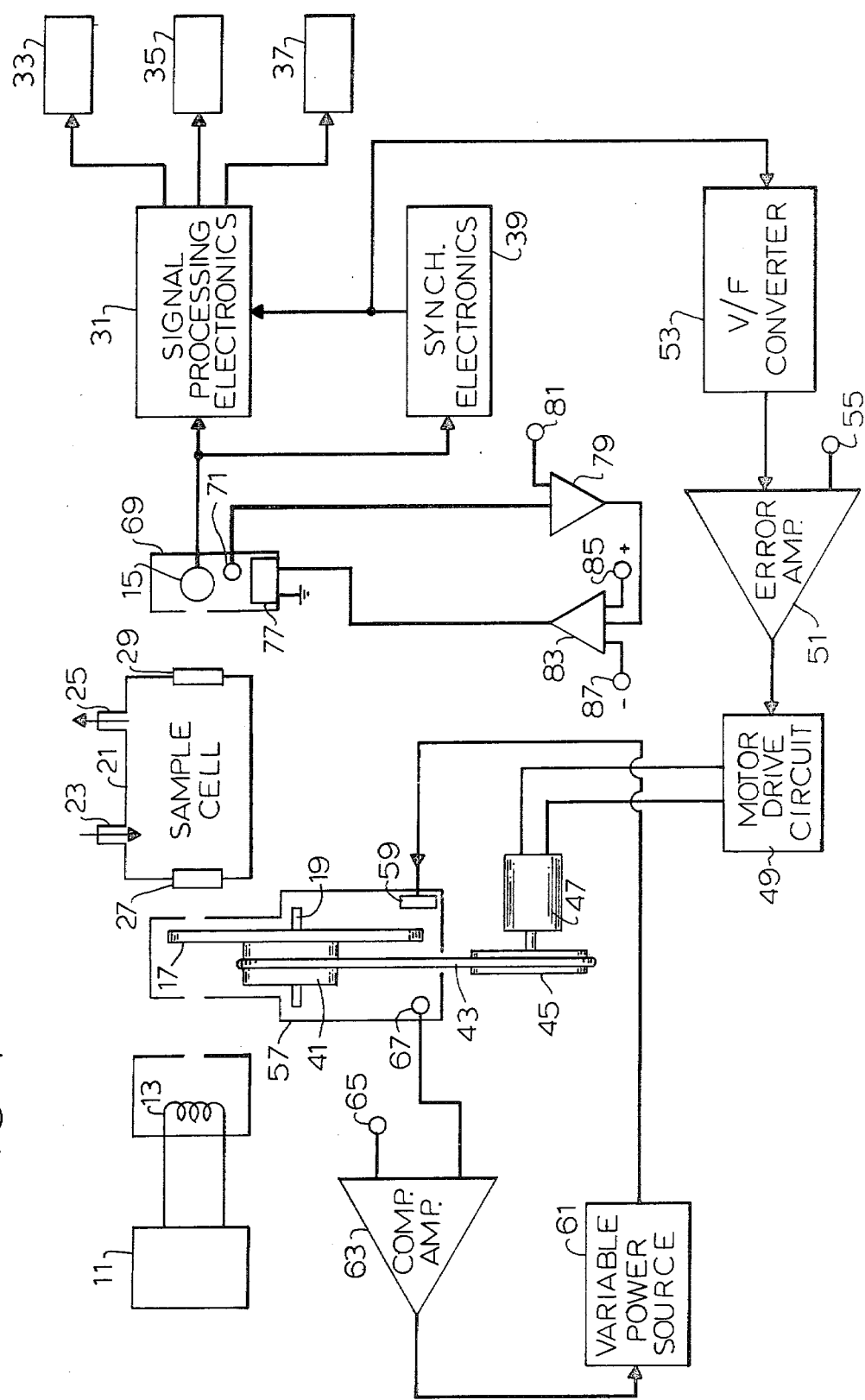
FIG. 1 is a schematic block diagram of a gas analyzer constructed in accordance with the invention.

Referring now more particularly to FIG. 1, a schematic block diagram of the system of the present invention may be seen. A power source 11 provides power to an infrared source 13. The source 13 is located at one end of an infrared optical path which terminates at the other end at a detector 15. In line in this optical path is a rotating filter wheel 17 rotating on an axle 19 parallel to and displaced from the optical path. The energy emitted by the source 13 passes the filter wheel 17 and enters a sample cell 21 through which the gas mixture being analyzed is passed. Gas enters the sample cell through an inlet port 23 and exits the sample cell through an outlet port 25. Infrared transparent windows 27 and 29 are provided at opposite ends of the sample cell in the optical path so that infrared energy may pass through the gas contained in the sample cell and be detected by the detector 15. The detector 15, which may be of the lead-selenide type, produces an electrical signal representative of the infrared energy which it detects.

The filter wheel 17, as is known in the art, carries a plurality of filters, each of which corresponds to the characteristic absorption wavelength of a particular gas being analyzed for. For example, if carbon dioxide is to be detected, a filter having a wavelength region centered around 4.2 microns would be utilized in the filter wheel. In addition, a reference filter may be used having a wavelength centered close to but not overlapping with the wavelength of any of the gases present in the sample gas. As a result, the signal detected by the detector 15 will be a series of pulses, each pulse occurring when a particular filter is interposed in the path of the infrared energy. Between filters, the detected signal may drop to a background level and a sample of the background level may also be utilized in the processing electronics.

The output of the detector 15 is applied to the signal processing electronics 31. The signal processing electronics may be of any suitable design, analog or digital, which will produce an output indicating the concentration of the sought constituents of the gas mixture in the sample cell 21. As the reference filter is aligned in the optical path, a measure of the basic sensitivity of the system to infrared radiation in general is obtained, including any attenuation of radiation by non-spectral contamination and the like on the infrared transparent windows of the sample cell. The sensitivity of the detector and the gain of the processing electronics may also be taken into account by this reference measurement. Each of the other filters provides radiation which ideally can only be absorbed if the specific gas to be detected through the use of that particular filter is present. Because these signals are affected by non-spectral contamination and the like identically with the reference signal, the reference signal can be used to minimize the effect of such phenomena. Because various signal processing techniques are well known in the prior art, further description of the signal processing electronics 31 will not be provided.

The output of the signal processing electronics is applied to the indicators 33, 35, and 37. The indicators may be of any suitable design. Each of the indicators corresponds to a particular gas being analyzed for. Although three indicators are shown, it will be apparent that any number may be utilized.

Figure 5:
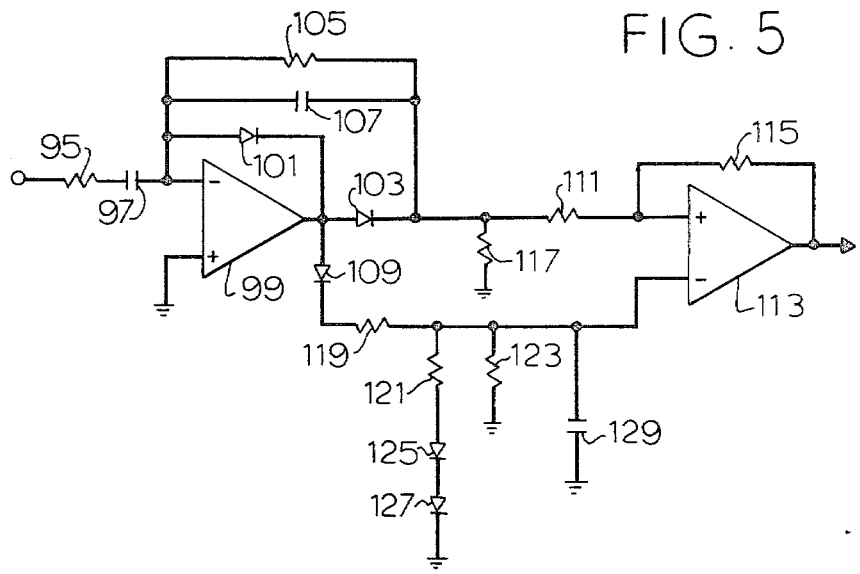
FIG. 5 is a circuit diagram of one form of synchronizing electronics which may be utilized in the analyzer of FIG. 1.

In order to provide information for the signal processing electronics 31 to enable same to properly synchronize with the position of the filter wheel 17, and thus synchronize with the proper wavelength being transmitted, the synchronizing electronics 39 are provided. Unlike many prior art systems, wherein synchronization with the rotary filter wheel 18 is obtained by photoelectric or electromechanical sensors related directly to the filter wheel, the illustrated embodiment of FIG. 1 employs a synchronizing electronics circuit 39 which derives a series of synchronizing pulses directly from the signal provided by the output of the detector 15. A specific circuit for accomplishing this is shown in FIG. 5 and will be described in detail subsequently herein.

In the illustrated embodiment, the synchronizing signal output of the synchronizing electronics 39 is not only applied to the signal processing electronics 31, but is also applied to a servo-control loop for controlling the speed of the rotary filter wheel in accordance with the synchronizing pulses. As is illustrated in the drawing, the rotary filter wheel 17 is driven on the axle 19 by a drum 41 and drive belt 43. The drive belt 43 passes around the drum 41 and around a pulley 45 which is driven by a suitable motor 47. Power for the motor 47 is provided by a motor drive circuit 49 which is voltage sensitive to regulate the speed of the motor 47. Such motor drive circuits are well known in the art and will therefore not be described further herein.

Voltage is applied to the motor drive circuit from an error amplifier 51. One input of the error amplifier is supplied by a frequency to voltage converter 53. The other input to the error amplifier is provided by a reference voltage source 55. Synchronizing pulses from the synchronizing electronics 39 are applied to the frequency to voltage converter 53, which provides a voltage signal output representative of the frequency of the synchronizing pulses. This voltage output is applied to the error amplifier, and the difference signal from the reference voltage is applied to the motor drive circuit to appropriately vary the speed of the motor 47. Accordingly, the detector optical pulse signal is utilized as the original source feedback information for control of the speed of the rotary filter wheel.

For any given gas to be detected, a change in ambient temperature affecting the temperature of the various components of the system may significantly affect system stability. The location of the wavelength of the filters naturally affects the system stability. For a given change in any or all of the wavelengths being transmitted, the resulting accuracy of the system will be affected, a phenomenon known as zero drift.

In order to provide temperature stability for the rotary filter wheel, an enclosure 57 is provided surrounding the rotary filter wheel. The enclosure 57 may include openings or transparent windows to allow passage of the infrared energy, and may also provide suitable openings for the belt 43. Inside the enclosure 57, a heater 59 is positioned. A variable power source 61, positioned outside the enclosure 57, is electrically connected to the heater 59 in order to provide power thereto. Connected to the variable power source is a comparator amplifier 63. One input of the comparator amplifier is connected to a temperature reference voltage 65, and the other is connected to a temperature sensor 67, for example a suitable thermistor. The temperature reference voltage at the terminal 65 may be provided by a fixed resistor or the like, and the comparator amplifier servos the power delivered to the heater 59 to maintain the temperature sensor 67 at a constant temperature. In this manner, the temperature of the filter wheel 17 is maintained constant, minimizing the effects of zero drift.

In order to stabilize the output signal of the detector 15, as is known in the prior art, the temperature of the detector is maintained constant. Prior art techniques for accomplishing this typically have included means for cooling the detector to a level substantially below room temperature, or heating the detector substantially above room temperature. This unidirectional form of temperature regulation sometimes requires relatively large amounts of power, particularly where ambient temperature is high.

In accordance with one aspect of the present invention, the detector 15 is maintained at a preselected temperature, for example room temperature, and is either cooled down or heated up from the ambient temperature as is necessary to maintain the preselected temperature. To this end, the detector 15 is provided with a suitable housing 69 within which is mounted a thermistor or temperature transducer 71 and a thermoelectric heater-cooler 77. Thermistors and thermoelectric heater-coolers are well known in the art and will not be described further herein. The output of the thermistor or temperature transducer 71 is applied to a comparator amplifier 79. The other input of the comparator amplifier is connected to a reference voltage 81. The comparator or error amplifier amplifies the difference between the two signals and applies it to the bidirectional power amplifier 83. The amplifier 83 may be of any suitable type known in the art, and has one input connected to a positive voltage source 85 and another input connected to a negative voltage source 87. Depending upon the output of the comparator 79, the amplifier 83 causes the thermoelectric heater-cooler 77 to either increase or decrease the temperature of the detector 15 and the thermistor 71 within the housing 69 and therefore regulate the temperature of the detector 15. In this way, less power is required to maintain a constant temperature in the detector 15 than is typical of prior art devices. Because less cooling or heating effectiveness is required, the illustrated and described arrangement for maintaining constant detector temperature is also significantly lower in cost from typical prior art systems.

Figure 2:
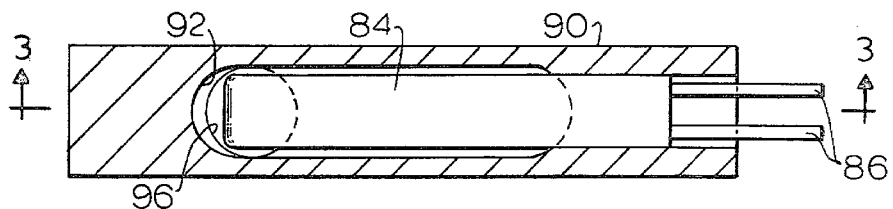
FIG. 2 is a full section view of an infrared source which may be employed in the analyzer of FIG. 1.
Figure 3:
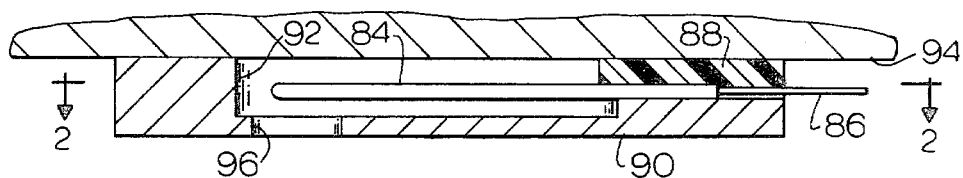
FIG. 3 is a cross-sectional view taken along the line 3—3 of FIG. 2.

In a preferred form of the invention, the infrared source 13 comprises an indirectly heated encapsulated tungsten metallized ceramic heater. The details of the tungsten heater source are shown in FIGS. 2 and 3. The tungsten heater 84 is screen printed on alumina sheets and coated with a layer of insulating material. The assembly is then sintered at high temperature to produce a monolithic structure. The leads 86 protrude from one end and the structure is mounted by a high temperature epoxy block 88 in a metal block 90. The metal block has a suitably shaped recess 92 to avoid contact with the heater 84, and is mounted to a heat sink 94 by means not shown. A window 96 is provided communicating with the recess 92 and through which the infrared energy passes to the detector.

One potential drawback is maintaining the detector 15 at or near room temperature as above described is in the variation of detector response with wavelength. For example, the typical lead-selenide detector has a response at carbon monoxide wavelengths which is much less than the response at hydrocarbon wavelengths. Although this difference may be lessened by cooling the detector to 0° C. or lower, the cost saving advantages described above are no longer available. Differences in pulse amplitudes may be accommodated by suitably constructing the signal processing electronics 31. However, this may significantly increase the costs of the electronics.

In accordance with the present invention, the infrared source 13 employs as the characteristic that its emissivity varies with the wavelengths in such a way as to at least partially compensate for the wavelength dependence of the response of the detector 15. By way of example, a typical infrared source may have a variation in emissivity with wavelength which is close to negligible. However, the variation of the response of a lead-selenide detector with wavelength may be as great as 60%, as is the case between HC and CO. In accordance with one aspect of the present invention, the infrared source 13 is selected to have an emissivity which varies substantially inversely in relation to the variation in response of the detector with wavelength. An example of such an infrared source is the ceramic heater available from Kyocera International Incorporated of Cupertino, Calif. This heater, for example, has an emissivity of 0.5 for CO and an emissivity of 0.2 for HC at a temperature of 800° C. Another advantage of this particular heater is its relatively high temperature and large fraction of the emitter at the desired high temperature at wavelengths greater than 4.3 micrometers. In this range, the variation in emission with wavelength is minimized.

The fraction of radiation at a given wavelength that is absorbed by a fixed concentration of gas in the sample cell 21 will change if the temperature of the gas changes or if the interference filter in the filter wheel 17 does not completely cover the absorption band and either the filter or the gas temperature is allowed to change. Temperature stabilization of the filter wheel has been described above. In accordance with one aspect of the present invention, the temperature dependence of the absorption of the gas in the sample cell 21 at any given wavelength is compensated for by adding temperature sensitive resistor means, appropriately calibrated, in the signal processing means. Such temperature sensitive resistor means may be utilized to vary the gain of the signal processing means, such as by making the signal processing electronics temperature dependent and equal in magnitude, but opposite in sign, to that of the absorbed gaseous signal. On the other hand, provision may also be made to provide an electronic test signal for periodic calibration of the device whose value is temperature dependent in a way that is identical to that of the absorbed gaseous material. The span calibration may then be adjusted by the operator of the device to make the gain of the signal processing electronics agree with the test signal at each temperature.

Figure 4:
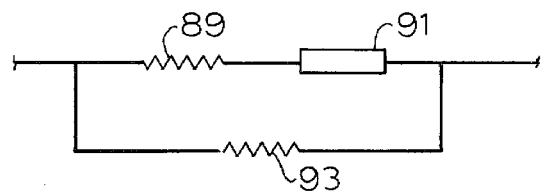
FIG. 4 is a temperature stabilizing network which may be utilized in the gas analyzer of FIG. 1.

To this end, a network may be incorporated in either the signal processing electronics or the calibration electronics thereof as shown in FIG. 4. In FIG. 4, a resistor 89 is series connected with a thermistor 92. A resistor 93 is connected across the series combination of the resistor 89 and thermistor 91. The network shown in FIG. 4 may be used to replace a suitable resistor in the processing electronics. For example, one of the gain determining resistors of the amplifiers may be replaced. Alternatively, a resistor in the electronic test signal network, not shown in detail but incorporated in the processing electronics, may be replaced by the thermistor network of FIG. 4. Depending upon the location selected for the thermistor network of FIG. 4, one network may be needed for each gas, or a single network may suffice.

Referring now to FIG. 5, one particular circuit which may be utilized as the synchronizing electronics 39 for developing a series of synchronizing pulses directly from the detector output is illustrated. A resistor 95 and capacitor 97 are series connected between the output of the detector and the negative input of an amplifier 99. A diode 101 is connected across the negative input and the output of the amplifier 99 and the positive input of the amplifier 99 is grounded. A diode 103 is connected in series with the output of the amplifier 99, and a resistor 105 and capacitor 107 are connected in parallel with each other across the series combination of the amplifier 99 and the diode 103. A diode 109 is also series connected with the output of the amplifier 99. The combination of the resistor 95 and 105, the capacitors 97 and 107, and the diodes 101, 103 and 109, together with the amplifier 99, forms a unique circuit that combines a low pass filter, a differentiator, and two half-wave precision rectifier functions utilizing just a single operational amplifier.

The diode 103 is series connected through a resistor 111 to the positive input of a discriminator amplifier 113. A resistor 115 is connected to the operational amplifier 113, and a load resistor 117 is connected from the junction between the diode 103 and the resistor 111 to ground. The resistor 117, resistor 111, resistor 115, and the operational amplifier 113 together form a comparator.

The function of a floating threshold network is performed by resistors 119, 121, and 123, diodes 125 and 127, and capacitor 129. The resistor 119 is series connected between the diode 109 and the negative input of the operational amplifier 113. The resistor 121 is connected in series with the diodes 125 and 127 from the junction between the resistor 119 and the amplifier 113 to ground. The resistor 123 is connected in parallel with the combination of the resistor 121 and diodes 125 and 127. The capacitor 129 is connected in parallel with the resistor 123. The resistor 119 attenuates the output of the amplifier 99, as does the resistor 123. On the rising edge of the output signal of the amplifier 99, the capacitor 129 follows the increasing signal or positive output.

The capacitor 129, together with the resistors 119 and 123 also serves as an R-C network which delays the decay time of the signal. As soon as the inputs to the amplifier 113 change in relationship (one becomes greater than the other), the diode 109 acts as a switch, in effect turning off the amplifier because of reverse bias. This makes the decay rate dependent on the amplitude of the derivative of the detector output. Thus, the threshold or switch point floats in accordance with the amplitude of the derivative signal, making it independent of the maximum amplitude of the pulses in the output of the detector.

It may be seen, therefore, that the invention provides an improved gas analyzer of the non-dispersive infrared type wherein temperature stability is provided, span stabilization is readily accomplished, and zero drift is minimized. Various modifications of the invention in addition to those shown and described herein will become apparent to those skilled in the art from the foregoing description and accompanying drawings. Such modifications are intended to fall within the scope of the appended claims.

What is claimed is:

1. A gas analyzer comprising, a sample cell for containing gas to be analyzed, means for producing and directing infrared energy through said sample cell, means for detecting the infrared energy passing through said sample cell and producing an electrical signal representative thereof, means coupled to said detecting means for processing the electrical signal to produce an output indicating the concentration of the constituents of the gas in said sample cell, a rotary filter wheel for successively and repetitively positioning at least one filter in the path of the infrared energy, a housing enclosing said filter wheel exclusive of said sample cell and said detecting means, means for maintaining the temperature in said housing at a substantially constant level, said signal processing means including means for compensating the output thereof for variation in the absorption characteristic of gas with temperature.

2. A gas analyzer according to claim 1 wherein said detecting means include a lead-selenide detector, and wherein said infrared energy producing and directing means include an infrared energy source having an emissivity characteristic which varies such as to substantially compensate for wavelength dependence of the response of lead-selenide.

3. A gas analyzer according to claim 1 including means coupled to said detector means for deriving a series of synchronizing pulses related to variations in the electrical signal produced by said detector means, and servo-control means controlling the speed of said rotary filter wheel in accordance with said synchronizing pulses.

4. A gas analyzer according to claim 2 including thermoelectric means for maintaining the temperature of said detector means at a preselected level, means for sensing the temperature of said detector means, and bidirectional power supply means for said thermoelectric means responsive to said temperature sensing means for causing said thermoelectric means to heat or cool said detector means in relation to ambient temperature.

5. A gas analyzer according to claim 1 wherein said compensating means include temperature sensitive resistor means for varying the gain of said signal processing means.

6. A gas analyzer according to claim 1 wherein said compensating means include temperature sensitive resistor means for varying the calibration of said signal processing means.

7. A gas analyzer, comprising, a sample cell for containing gas to be analyzed, means for producing and directing infrared energy through said sample cell, lead-selenide detector means for detecting the infrared energy passing through said sample cell and producing an electrical signal representative thereof, means coupled to said detector means for processing the electrical signal to produce an output indicating the concentration of the constituents of the gas in said sample cell, a rotary filter wheel for successively and repetitively positioning at least one filter in the path of the infrared energy, said infrared energy producing and directing means including an infrared energy source having an emissivity characteristic which varies such as to at least partially compensate for wavelength dependence of the response of lead-selenide, thermoelectrical means for maintaining the temperature of said detector means at a preselected level, means for sensing the temperature of said detector means, and bidirectional power supply means for said thermoelectric means responsive to said temperature sensing means for causing said thermoelectric means to heat or cool said detector means in relation to ambient temperature.

8. A gas analyzer comprising, a sample cell for containing gas to be analyzed, means for producing and directing infrared energy through said sample cell, detector infrared energy through said sample cell, detector means for detecting the infrared energy passing through said sample cell and producing an electrical signal representative thereof, means coupled to said detector means for processing the electrical signal to produce an output indicating the concentration of the constituents of the gas in said sample cell, a rotary filter wheel for successively and repetitively positioning at least one filter in the path of the infrared energy, means coupled to said detector means for deriving a series of synchronizing pulses related to variations in the electrical signal produced by said detector means, and servo-control means for controlling the speed of said rotary filter wheel in accordance with said synchronizing pulses.

9. A gas analyzer comprising, a sample cell for containing gas to be analyzed, means for producing and directing infrared energy through said sample cell, detector means for detecting the infrared energy passing through said sample cell and producing an electrical signal representative thereof, and means coupled to said detector means for processing the electrical signal to produce an output indicating the concentration of the constituents of the gas in said sample cell, said signal processing means including a thermistor network for compensating the output thereof for variation in the absorption characteristic of gas with temperature.

* * * * *

UNITED STATES PATENT AND TRADEMARK OFFICE
CERTIFICATE OF CORRECTION

PATENT NO. : 4,233,513

DATED : November 11, 1980

INVENTOR(S) : William L. Elder et al.

It is certified that error appears in the above—identified patent and that said Letters Patent is hereby corrected as shown below:

Column 6, line 39, "resistor" should read -- resistors --.

Column 8, line 9, delete the first comma.

Column 8, line 24, "thermoelectrical" should read -- thermoelectric --.

Column 8, lines 34 and 35, delete "detector infrared energy through said sample cell,".

Signed and Sealed this

Seventeenth Day of March 1981

[SEAL]

Attest:

RENE D. TEGTMEYER

Attesting Officer   Acting Commissioner of Patents and Trademarks